United States Patent
Lemoine et al.

(10) Patent No.: US 7,326,409 B2
(45) Date of Patent: Feb. 5, 2008

(54) DEODORANT COSMETIC COMPOSITION COMPRISING A COMBINATION OF ZINC PIDOLATE AND AN ANTIPERSPIRANT ALUMINUM SALT

(75) Inventors: Cyril Lemoine, Puiseux-en-France (FR); Nathalie Beau, Eragny-sur-Oise (FR); Estelle Prud'homme, Paris (FR)

(73) Assignee: L'Oreal S.A., Paris (FR)

( * ) Notice: Subject to any disclaimer, the term of this patent is extended or adjusted under 35 U.S.C. 154(b) by 584 days.

(21) Appl. No.: 11/009,130

(22) Filed: Dec. 13, 2004

(65) Prior Publication Data

US 2005/0163737 A1 Jul. 28, 2005

Related U.S. Application Data

(60) Provisional application No. 60/534,407, filed on Jan. 7, 2004.

(30) Foreign Application Priority Data

Dec. 12, 2003 (FR) .................... 03 51035

(51) Int. Cl.
*A61Q 15/00* (2006.01)
*A61K 8/00* (2006.01)
*A61K 8/04* (2006.01)

(52) U.S. Cl. .................... 424/65; 424/68; 424/400; 424/401

(58) Field of Classification Search ................ 424/65, 424/68, 400, 401
See application file for complete search history.

(56) References Cited

U.S. PATENT DOCUMENTS

| 3,792,068 A | 2/1974 | Luedders et al. |
| 4,822,596 A | 4/1989 | Callingham et al. |
| 5,643,559 A | 7/1997 | Eigen et al. |
| 6,403,067 B1 | 6/2002 | Schamper et al. |
| 6,426,061 B1 | 7/2002 | Li et al. |
| 6,632,421 B2 | 10/2003 | Ascione et al. |

FOREIGN PATENT DOCUMENTS

| DE | 101 37 901 A1 | 12/2002 |
| EP | 0 768 080 B1 | 4/1997 |
| FR | 2 815 856 | 5/2002 |
| JP | 62-289512 | 12/1987 |
| JP | 03-095111 | 4/1991 |
| WO | WO 97/14399 | 4/1997 |
| WO | WO 97/44010 | 11/1997 |
| WO | WO 00/68369 | 11/2000 |
| WO | WO 01/52804 A1 | 7/2001 |
| WO | WO 01/99376 A2 | 12/2001 |

OTHER PUBLICATIONS

English Abstract for JP 03-095111.
English Abstract for JP 62-289512.
English language Derwent Abstract of DE 101 37 901 A1, Dec. 5, 2002.
English language Derwent Abstract of FR 815 856, May 3, 2003.

*Primary Examiner*—Shelley A. Dodson
(74) *Attorney, Agent, or Firm*—Finnegan, Henderson, Farabow, Garrett & Dunner, L.L.P.

(57) ABSTRACT

The present disclosure relates to a deodorant cosmetic composition comprising: a) zinc pidolate and b) at least one antiperspirant aluminum salt, wherein the zinc pidolate/at least one aluminum salt weight ratio ranges from 1/200 to 10/1. The present disclosure also relates to a cosmetic process for treating human perspiration and human underarm odors with the composition disclosed herein.

29 Claims, No Drawings

DEODORANT COSMETIC COMPOSITION COMPRISING A COMBINATION OF ZINC PIDOLATE AND AN ANTIPERSPIRANT ALUMINUM SALT

This application claims benefit of U.S. Provisional Application No. 60/534,407, filed Jan. 7, 2004.

The present disclosure relates to a composition comprising: a) zinc pidolate and b) at least one antiperspirant aluminum salt, wherein the zinc pidolate/at least one aluminum salt weight ratio ranges from 1/200 to 10/1. In one embodiment the composition is a deodorant cosmetic composition.

The disclosure also relates to a cosmetic process for treating human perspiration and human underarm odors with the composition disclosed herein.

In the cosmetic field, it is a well-known practice to use, in topical application, deodorant products comprising active substances of antiperspirant type, of bactericidal type and/or of odor absorbent type to reduce or even eliminate the generally unpleasant underarm odors.

Bactericides may inhibit the growth of the skin flora that is responsible for underarm odors. They, however, have the drawback of not being active on the sweat odor already developed. Among the bactericidal products, the most commonly used is Triclosan (2,4,4'-trichloro-2'-hydroxydiphenyl ether), which modifies considerably the ecology of the skin flora and may be inhibited by certain compounds such as, for example, nonionic surfactants, which are commonly used in the formulation of cosmetic compositions. Furthermore, the insoluble nature of Triclosan in water does not allow it to be incorporated into essentially aqueous formulations.

Antiperspirant substances may have the effect of limiting the flow of sweat. They generally comprise aluminum salts. Their deodorant efficacy may be limited when they are used alone. Furthermore, in high concentrations, these substances may irritate the skin.

European Patent No. 768,080 discloses aqueous deodorant compositions, such as water/silicone emulsions containing as odor-absorbing active agent water-soluble zinc salts, for example, zinc pyrrolidonecarboxylate, also known as zinc pidolate, zinc sulfate, zinc chloride, zinc lactate, zinc pidolate, and zinc phenolsulfonate. Their deodorant efficacy may still not be fully satisfactory when they are used alone.

U.S. Pat. No. 6,426,061 also discloses compositions for combating the development of human skin perspiration odors, comprising the combination of the following active agents: (1) an androgen receptor inhibitor (for example, resveratrol, epigallocatechin 3-gallate or flufenamic acid); (2) an anti-DHT active agent (for example, zinc salts, such as zinc sulfate); (3) an inhibitor of odor-bearing proteins; (4) an antiperspirant aluminum salt; and (5) an antimicrobial agent such as chlorhexidine dipidolate or chlorhexidine diacetate. These compositions have the drawback of using antimicrobial agents that are particularly active on the cutaneous flora.

International Patent Application No. WO 01/52804 discloses deodorant compositions based on antiperspirant salts, to which it is proposed to add transition metal-chelating agents. These formulations may be potentially ecotoxic and may pose environmental problems.

International Patent Application No. WO 01/99376 also discloses deodorant compositions comprising arylsulfatase inhibitors, among which aluminum salts and zinc pidolate are mentioned. For example, an antiperspirant stick comprising 20% by weight of aluminum chlorohydrate and 0.05% of zinc pidolate. This type of composition may produce a high level of white residue on the skin after application.

Accordingly, the present disclosure relates to novel cosmetic compositions comprising a deodorant system whose efficacy may be higher than that of antiperspirant salts and than that of zinc salts used alone, and which do not have at least one drawback of the deodorant products of the prior art as mentioned above.

As such, the present disclosure provides a composition obtained by using a combination of zinc pidolate (or zinc pyrrolidonecarboxylate) and of at least one antiperspirant aluminum salt, wherein the zinc pidolate/at least one aluminum salt weight ratio ranges from 1/200 to 10/1.

In one embodiment, this particular combination may substantially increase the effect of reducing the odor intensity compared with the active agents used individually, and may even produce a synergistic effect.

In another embodiment, this particular combination may be formulated in cosmetically acceptable deodorant compositions whose levels of visible residue on the skin upon application or after drying of the composition after application are low and comparable with the deodorant products currently on the market.

A further embodiment of the present disclosure is a deodorant cosmetic composition comprising a) zinc pidolate and b) at least one antiperspirant aluminum salt, wherein the zinc pidolate/at least one aluminum salt weight ratio ranges from 1/200 to 10/1 and for example, from 1/20 to 5/1.

The present disclosure also relates to a cosmetic process for treating human perspiration and human underarm odors using the composition disclosed herein.

For the purposes of the present disclosure, the term "deodorant composition" means any composition capable of reducing the flow of sweat and of at least one of masking, absorbing, improving and/or reducing the unpleasant odor resulting from the decomposition of human sweat by bacteria.

As used herein, the term "antiperspirant aluminum salt" means any salt or any aluminum complex that has the effect of reducing or limiting the flow of sweat.

The at least one aluminum salt in accordance with the present disclosure may be, for example, chosen from aluminum halohydrates; aluminum zirconium halohydrates; and complexes of zirconium hydroxychloride and of aluminum hydroxychloride with an amino acid, such as those described in U.S. Pat. No. 3,792,068, which are commonly known as "ZAG complexes".

Among the aluminum salts that may be mentioned, for example, are aluminum chlorohydrate in activated or unactivated form, aluminum chlorohydrex, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichloro-hydrate, aluminum sesquichlorohydrex polyethylene glycol complex, aluminum sesquichlorohydrex propylene glycol complex, and aluminum sulfate buffered with sodium aluminum lactate.

Among the aluminum zirconium double salts that may be mentioned, for example, are aluminum zirconium octachlorohydrate, aluminum zirconium pentachloro-hydrate, aluminum zirconium tetrachlorohydrate, and aluminum zirconium trichlorohydrate. An example of an aluminum zirconium double salt is the product sold by the company Reheis under the name Reach AZP-908-SUF.

The complexes of zirconium hydroxychloride and of aluminum hydroxychloride with an amino acid are generally known under the name ZAG (when the amino acid is glycine). Among these products, mention may be made of the aluminum zirconium octachlorohydrex glycine, aluminum zirconium pentachlorohydrex glycine, aluminum zirconium tetrachlorohydrex glycine, and aluminum zirconium trichlorohydrex glycine complexes.

The at least one antiperspirant aluminum salt may be present in the composition according to the disclosure in an amount ranging from 0.5% to 25%, by weight relative to the total weight of the composition.

Zinc pidolate may be present in the composition according to the disclsoure in an amount ranging from 0.05% to 10%, by weight and for example, from 0.1% to 5%, by weight relative to the total weight of the composition.

The deodorant compositions according to the disclosure intended for cosmetic use may be in the form of lotions, creams or fluid gels distributed as an aerosol spray, in a pump-dispenser bottle or as a roll-on, in the form of thick creams distributed in tubes or a grille; in the form of wands (sticks), and may comprise in this regard the ingredients generally used in products of this type and well known to those skilled in the art, provided that they do not interfere with the aluminum salt and the zinc pidolate described in the present disclosure.

The deodorant compositions according to the present disclosure intended for cosmetic use may comprise at least one aqueous phase. They may be formulated, for example, in a form chosen from aqueous lotions, water-in-oil emulsions, oil-in-water emulsions, and multiple emulsions (oil-in-water-in-oil and water-in-oil-in-water triple emulsions (such emulsions are known and described, for example, by C. F. Fox in "Cosmetics and Toiletries", November 1986, Vol. 101, pages 101-112)).

The at least one aqueous phase of the disclosed composition comprises water and generally other water-soluble or water-miscible solvents. The water-soluble or water-miscible solvents may be chosen from short-chain monoalcohols, for example, monoalcohols of $C_1$-$C_4$, such as ethanol and isopropanol; diols and polyols, for example, ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol. For example, propylene glycol and glycerol may be used.

According to one embodiment of the present disclosure, the antiperspirant compositions may be anhydrous.

For the purposes of the disclosure, the term "anhydrous" means a composition whose content of free or added water is less than 3% and for example, whose content of added water is less than 1%, by weight relative to the total weight of the composition.

The compositions according to the disclosure, for example, comprise at least one water-immiscible organic liquid phase. The at least one water-immiscible organic phase generally comprises at least one hydrophobic compound that renders the phase water-immiscible. The at least one water-immiscible organic phase is liquid (in the absence of a structuring agent) at room temperature (20°-25° C.). The at least one water-immiscible organic liquid phase in accordance with the disclosure is chosen from an oil and a mixture of oils and comprises at least 80% of compounds with a vapor pressure not exceeding 4 kPa (30 mmHg) at 25° C.

The at least one water-immiscible organic liquid phase, for example, comprises at least one emollient oil chosen from volatile and non-volatile, silicone-based, and hydrocarbon-based emollient oils. These emollient oils are, for example, described in U.S. Pat. Nos. 4,822,596 and 4,904,463.

As used herein, volatile silicones are defined, in a known manner, as being compounds that are volatile at room temperature. Mention may be made, for example, among these compounds, to cyclic and linear volatile silicones of the dimethylsiloxane type whose chains comprise from 3 to 9 silicone-based residues. Cyclomethicones $D_4$, $D_5$ and $D_6$ may, for example, be used.

As used herein, non-volatile silicones are defined, in a known manner, as being compounds with a low vapor pressure at room temperature. The following may be included among these compounds: polyalkylsiloxanes, such as linear polyalkylsiloxanes, for example, the linear polydimethylsiloxanes, or dimethicones, sold by the company Dow Corning under the name "Dow Corning 245 Fluid"; polyalkylarylsiloxanes, for example, the polymethylphenylsiloxanes sold by the company Dow Corning under the name "Dow Corning 556 Fluid"; and copolymers of polyether and siloxane, for example, dimethicone copolyols.

Among the non-volatile emollient oils that may be used in the present disclosure, examples that may be mentioned include: hydrocarbon-based derivatives, mineral oils, fatty alcohols, esters of $C_3$-$C_{18}$ alcohols with $C_3$-$C_{18}$ acids, esters of benzoic acid with $C_{12}$-$C_{18}$ alcohols and mixtures thereof, $C_2$-$C_6$ polyols, for example, chosen from glycerol, propylene glycol or sorbitol, polyalkylene glycol polymers.

The at least one emollient oil may be present in an amount ranging from 1% to 50%, by weight and for example, from 5% to 40%, by weight relative to the total weight of the composition.

The deodorant cosmetic composition according to the present disclosure may comprise at least one additional deodorant active agent chosen from, for example, bacteriostatic agents and bactericidal agents such as 2,4,4'-trichloro-2'-hydroxydiphenyl ether (Triclosan), 2,4-dichloro-2'-hydroxydiphenyl ether, 3',4',5'-trichlorosalicylanilide, 1-(3',4'-dichlorophenyl)-3-(4'-chlorophenyl)urea (Triclocarban) and 3,7,11-trimethyldodeca-2,5,10-trienol (Farnesol); quaternary ammonium salts, for example, cetyltrimethylammonium salts and cetylpyridinium salts; chlorhexidine and salts; diglyceryl monocaprate, diglyceryl monolaurate and glyceryl monolaurate; and polyhexamethylene biguanide salts.

In order to improve the homogeneity of the product, it may be possible to use at least one suspension agent, for example, chosen from hydrophobic-modified montmorillonite clays, for example, hydrophobic-modified bentonites and hectorites. Examples that may be mentioned include the product stearalkonium bentonite (CTFA name) (product of reaction of bentonite and the quaternary ammonium stearalkonium chloride), such as the commercial product sold under the name Tixogel MP 250 by the company Sud Chemie Rheologicals, United Catalysts Inc. or the product disteardimonium hectorite (CTFA name) (product of reaction of hectorite and of distearyldimonium chloride) sold under the name Bentone 38 or Bentone Gel by the company Elementis Specialities.

The at least one suspension agent is present in an amount ranging from 0.1% to 5%, by weight and for example, from 0.2% to 2%, by weight relative to the total weight of the composition.

The compositions according to the disclosure may also comprise at least one organic powder.

Among the fillers that may be used according to the disclosure, mention may be made of organic powders. As used herein, the term "organic powder" means any solid that is insoluble in the medium at room temperature (25° C.).

The at least one organic powder that may be used in the composition of the disclosure, include, for example, polyamide particles and for example, those sold under the name Orgasol by the company Atochem; polyethylene powders; microspheres based on acrylic copolymers, such as those made of ethylene glycol dimethacrylate/lauryl methacrylate copolymer, sold by the company Dow Corning under the name Polytrap; polymethyl methacrylate microspheres, sold under the name Microsphere M-100 by the company Matsumoto or under the name Covabead LH85 by the company Wackherr; ethylene-acrylate copolymer powders, for example, those sold under the name Flobeads by the company Sumitomo Seika Chemicals; expanded powders such as hollow microspheres and for example, microspheres formed from a terpolymer of vinylidene chloride, of acrylonitrile and of methacrylate and sold under the name Expancel by the company Kemanord Plast under the references 551 DE 12 (particle size of about 12 μm and density of 40 kg/m$^3$), 551 DE 20 (particle size of about 30 μm and a density of 65 kg/m$^3$) and 551 DE 50 (particle size of about 40 μm), or the microspheres sold under the name Micropearl F 80 ED by the company Matsumoto; powders of natural organic materials such as starch powders, for example, of corn starch, wheat starch or rice starch, which may or may not be crosslinked, such as the starch powder crosslinked with octenylsuccinate anhydride, sold under the name Dry-Flo by the company National Starch; silicone resin microbeads such as those sold under the name Tospearl by the company Toshiba Silicone, such as Tospearl 240; amino acid powders such as the lauroyllysine powder sold under the name Amihope LL-11 by the company Ajinomoto; particles of wax microdispersion, which for example, have mean sizes of less than 1 μm and for example, range from 0.02 μm to 1 μm, and which consist essentially of a wax or a mixture of waxes, such as the products sold under the name Aquacer by the company Byk Cera, and for example, Aquacer 520 (mixture of synthetic and natural waxes), Aquacer 514 or 513 (polyethylene wax), Aquacer 511 (polymer wax), or such as the products sold under the name Jonwax 120 by the company Johnson Polymer (mixture of polyethylene wax and paraffin wax) and under the name Ceraflour 961 by the company Byk Cera (micronized modified polyethylene wax); and mixtures thereof.

The cosmetic composition according to the disclosure may also comprise at least one cosmetic adjuvant chosen from waxes, softeners, antioxidants, opacifiers, stabilizers, moisturizers, vitamins, fragrances, bactericides, preserving agents, polymers, fragrances, thickeners, propellants, or any other ingredient usually used in cosmetics for this type of application.

Needless to say, a person skilled in the art will take care to select this or these optional additional compound(s) such that the advantageous properties intrinsically associated with the cosmetic composition in accordance with the disclosure are not, and are not substantially, adversely affected by the envisaged addition(s).

The waxes may be chosen from animal, fossil, plant, mineral and synthetic waxes. Mention may be made, for example, to beeswaxes, carnauba wax, candelilla wax, sugar cane wax, Japan wax, ozokerites, montan wax, microcrystalline waxes, paraffins, and silicone waxes and resins.

The thickeners, which are, for example, nonionic, may be chosen from modified and unmodified guar gums and celluloses, such as hydroxypropyl guar gum and cetylhydroxyethylcellulose, silicas, such as Bentone Gel MIO sold by the company NL Industries, and Veegum Ultra sold by the company Polyplastic.

The amounts of these various constituents, i.e., optional cosmetic adjuvants, that may be present in the cosmetic composition according to the disclosure are those conventionally used in deodorant compositions.

The compositions according to the disclosure may also contain at least one other agent for structuring or gelling the at least one water-immiscible organic liquid phase of the composition chosen from linear solid fatty alcohols and waxes; fatty acids and salts thereof (stearic acid, sodium stearate or 12-hydroxystearic acid; dibenzylidene alditols (DBS); lanosterol, N-acylamino acid derivatives; di- and tricarboxylic acid derivatives, such as alkyl-N,N'-dialkyl-succin-amides (i.e., dodecyl-N,N'-dibutylsuccinamide); elastomeric polyorganosiloxanes such as, those described in International Patent Application No. WO 97/44010.

The composition according to the disclosure may also be pressurized and may be packaged in an aerosol device.

The present disclosure is further related to an aerosol device comprising a container comprising a composition as defined above, at least one propellant and a device for distributing the aerosol composition.

The at least one propellant generally used in products of this type, which are well known to those skilled in the art, are, for example, dimethyl ether (DME); volatile hydrocarbons such as n-butane, propane or isobutane, and mixtures thereof, optionally with at least one chlorohydrocarbon and/or fluorohydrocarbon; among the latter, mention may be made of the compounds sold by the company Dupont de Nemours under the names Freon® and Dymel®, and for example, monofluorotrichloromethane, difluorodichloromethane, tetrafluorodichloroethane and 1,1-difluoroethane sold, for example, under the trade name Dymel 152 A by the company Dupont. Carbon dioxide, nitrous oxide, nitrogen or compressed air may also be used as the at least one propellant.

The composition comprising the deodorant composition and the at least one propellant may be in the same compartment or in different compartments in the aerosol container. According to the disclosure, the concentration of propellant generally ranges from 5% to 95% by pressurized weight and for example, from 50% to 85%, by weight relative to the total weight of the pressurized composition.

The distribution device, which forms a part of the aerosol device, generally comprises a distribution valve controlled by a distribution head, itself comprising a nozzle via which the aerosol composition is vaporized. The container comprising the pressurized composition may be opaque or transparent. It may be made of glass, of polymeric material or of metal, optionally coated with a coat of protective varnish.

The present disclosure further relates to a cosmetic process for treating human underarm odors comprising applying to the underarm area an effective amount of a composition as defined above.

Other than in the operation examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that numerical ranges and parameters setting forth the broad scope of the disclosure are approximations, the numerical values set forth in the specific examples are reported to as precisely as possible. Any numerical value, however, inherently contains certain errors necessarily resulting from the standard deviation found in their respective testing measurements.

The examples that follow serve to illustrate the present disclosure.

I. Comparison of the Deodorant Activity of the Zinc Pidolate/Aluminum Salt Combination Relative to the Triclosan/Aluminum Salt and Zinc Ricinoleate/Aluminum Salt Combinations Protocol of the Deodorant Efficacy Test Collections of underarm sweat were taken in a sauna from 6 volunteers; the samples of individual sweat, were stored in ice for a few hours, and were at this point virtually odorless. They were then mixed together and divided into 1 ml aliquots. The active agents were added to these aliquots, which were then incubated in an oven at 37° C. After incubation for 24 hours, a panel of experts evaluated the intensity of the odor in comparison with a control sample: 1 ml of sweat incubated without agent.

The results were expressed as a percentage of variation of the intensity of the odor in comparison with the control sweat sample (mean of the percentages of variation at T24h).

| Active Agents Tested | Amount Tested (mg AM/ml of sweat) | % of Reduction in the Intensity of the Odor |
|---|---|---|
| ACH | 0.1 mg AM | −37% |
| (A) | 0.1 mg AM | −47% |
| (B) | 0.4 mg AM | −49% |
| (C) | 0.3 mg AM | −4% |
| ACH + (A) | 0.2 mg AM | −72% |
| ACH + (B) | 0.5 mg AM | −46% |
| ACH + (C) | 0.4 mg AM | −38% |

ACH: aluminum chlorohydrate (Micro Dry - Reheis)
(A): zinc pidolate (Govobio G Zn - SEPPIC)
(B): Triclosan (Ciba)
(C): zinc ricinoleate (Grillo Werke)

It was found that the addition of zinc pidolate to the aluminum salt leads to a substantial increase in the effect of reducing the intensity of the odor, in contrast to the addition of Triclosan and that of zinc ricinoleate to the same aluminum salt.

| Active Agents tested | Amount Tested (mg AM/ml of sweat) | % of Reduction in the Intensity of the Odor |
|---|---|---|
| ACH | 0.2 mg AM | −47% |
| (A) | 0.2 mg AM | −47% |
| 0.1 mg ACH + 0.1 mg (A) | 0.2 mg AM | −72% |

It was found that the zinc pidolate/aluminum salt combination in a total amount of active agent of 0.2 mg lead to a substantial increase in the effect of reducing the intensity of the odor relative to each active agent used alone in the same amount. Synergism of the deodorant activity was thus observed.

II. Microbiological Test: Sparingly Bactericidal Activity of Zinc Pidolate Compared with Triclosan Protocol:

The test described herein allowed for a quantitative determination of the bactericidal activity of a composition on microorganisms under optimum growth conditions, i.e. microorganisms of the type *Corynebacterium xerosis* (Institut Pasteur Collection No. 5216); *Staphylococcus hominis* (Institut Pasteur Collection No. 81 57) and *Brevibacterium epidermidis* (Institut Pasteur Collection No. 102110), cultured on a gradient of tryptocasein soybean agar. On the day before the test, 32 g of tryptocasein soybean broth were placed in a pill bottle and incubated at 35° C. On the day of the test, 4 g of the test composition were added and the mixture was homogenized using a vortex mixer.

A growth control without product was prepared under the same conditions in order to check that the microorganisms were under favorable growth conditions throughout the test.

For the preparation of the inoculum, five days before the start of the test, two bacterial strains were subcultured on suitable medium. They were incubated for 5 days at 35° C. On the day of the test, the slope was washed with about 9 ml of diluent. The suspension obtained had a titre of 108 microorganisms/ml (counting was performed). 4 ml of inoculum were introduced into the pill bottle, which corresponded to a content of 107 bacteria per gram of preparation. The pill bottle was placed in an incubator-shaker (35° C.-200 rpm).

After each contact time (2, 4, 6 and 24 hours), the contents of the pill bottle were homogenized using the vortex mixer. Tenfold dilutions were prepared. They were applied to the surface of agar Petri dishes (Eugon LT 100 medium). The Petri dishes were incubated for 6 to 7 days in an oven at 35° C.

The colonies on the dishes containing more than 20 and fewer than 200 colonies were counted.

A Formulation 1 with zinc pidolate and a Formulation 2 with Triclosan were prepared; the supports were chosen so as to be compatible with the deodorant active agent.

| Ingredients | Formulation 1 (invention) | Formulation 2 (prior art) |
|---|---|---|
| Triclosan | — | 0.1 g |
| Zinc pidolate | 1 g | — |
| Polyethylene glycol 8 EO | 16.8 g | 6 g |
| Acrylic acid/$C_{10}$-$C_{30}$ alkyl acrylate crosslinked copolymer | — | 0.9 g |
| Pure sodium hydroxide | — | qs (pH = 7) |
| Microbiologically clean deionized water | 82.8 g | 93.0 g |

The bactericidal activity of each of the formulations, 1 and 2 with respect to the strains *Corynebacterium xerosis*, *Staphylococcus hominis* and *Brevibacterium* epidermidis, was measured and was compared with a formulation free of active agent (placebo). The results obtained were summarized in the following table:

| | Efficacy at 24 hours (relative to the gel free of active agent) | | |
|---|---|---|---|
| Compositions Strains | *Corynebacterium xerosis* (CIP 5216) | *Staphylococcus hominis* | *Brevibacterium epidermis* |
| 1 (invention) | zero | low | zero |
| 2 (prior art) | excellent | — | — |

Identical results: zero,
1 log of reduction: low,
2 log of reduction: moderate,
3 log of reduction: good,
≧4 log of reduction: excellent.

It was observed that in Formulation 1, the zinc pidolate used at a concentration 10 times higher than that of the Triclosan had low or zero antibacterial activity on the various strains tested. It thus had a substantially narrower spectrum of bactericidal activity than that of Triclosan and showed greater respect for the cutaneous flora.

III. Comparison of the Deodorant Activity of an Anhydrous Aerosol Based on Zinc Pidolate in Combination with an Aluminum Salt, Relative to an Aerosol Based on an Aluminum Salt—In Vivo Test The improvement in the deodorant efficacy of aluminum chlorohydrate in combination with zinc pidolate was confirmed in vivo on an antiperspirant anhydrous aerosol formulation. Formulation 3 according to the disclosure (combination of a zinc pidolate with an aluminum chlorohydrate in a 1/9.5 weight ratio) was compared with a Formulation 4 comprising only an aluminum salt (see table below).

| Ingredients | Formulation 3 (invention) | Formulation 4 (prior art) |
|---|---|---|
| Aluminum chlorohydrate (Micro Dry - Reheis) | 5.25 g | 5.25 g |
| Zinc pidolate | 0.50 g | — |
| Isopropyl palmitate | 0.90 g | 0.90 g |
| Triethyl citrate (Citroflex - Morflex) | 1.05 g | 1.05 g |
| Cyclopentasiloxane (DC245 - Dow Corning) | 5.56 g | 5.56 g |
| Cyclopentasiloxane and Dimethiconol (85.3/14.7) (DC1501 Fluid - Dow Corning) | 1.35 g | 1.35 g |
| Stearalkonium bentonite (Tixogel MP 250 - Sud Chemie Rheologicals United Catalysts Inc.) | 0.39 g | 0.39 g |
| Isobutane | 85.00 g | 85.00 g |

Protocol of the Deodorant Efficacy Test:

The tests were performed on 30 volunteers having a moderate and symmetrical odor intensity>5 on a scale from 1 (imperceptible intensity) to 9 (extremely strong intensity).

For each volunteer, one of the armpits was treated with a single application of Formulation 3, the other with Formulation 4.

The amount applied was 1.2±0.05 g vaporized 15 cm from the armpit. The deodorant was applied after wiping the armpit dry.

The evaluations were performed by means of a direct "sniff test" of the intensity of the perspiration odor and its unpleasantness, 24 hours after 1 application.

The deodorant efficacy was evaluated by means of the following two criteria:

(1) the intensity of the perspiration odor (scale from 1: imperceptible intensity to 9: extremely strong intensity); the smaller the value, the weaker the odor; and
(2) the hedonic value (scale from 1: extremely unpleasant odor, to 9: extremely pleasant); the higher the value, the smaller the unpleasantness.

The variation in the intensity of the odor of Formulation 3 according to the disclosure comprising the zinc pidolate/aluminum salt combination was measured relative to that of Formulation 4 not containing zinc pidolate.

% of variation=(value for Formulation 3–value for Formulation 4)×100/Formulation 4.

| Variation in the intensity of the odor | Variation in the hedonic value |
|---|---|
| −14% | +9% |

The data demonstrates that 24 hours after application, a significant reduction in the intensity of the underarm odor and a significant increase in the hedonic value, resulted in a reduction of the unpleasantness for the armpit treated with Formulation 3 according to the disclosure comprising the zinc pidolate/aluminum salt combination relative to Formulation 4 not containing zinc pidolate.

Formulations 5 and 6: Deodorant Sticks

| Ingredients | Formulation 5 (according to Example 1.5 of International Patent Application No. WO 01/99376) | Formulation 6 (invention) |
|---|---|---|
| Cyclopentasiloxane (DC245 - Dow Corning) | 23 g | 32 g |
| Hexyldecyl stearate (Eutanol G16S - Cognis) | 15 g | — |
| PPG-14 butyl ether (Ucon Fluid AP - Amerchol) | 5 g | 10 g |
| Hydrogenated castor oil (Cutina HR - Cognis) | 6 g | 4 g |
| Cetearyl alcohol (Lanette O - Cognis) | 8 g | — |
| Cetearyl alcohol/Ceteareth- 30 80/20 (Sinnowax AO - Cognis) | 15 g | — |
| Talc | 8 g | 2 g |
| Aluminum chlorohydrate (Micro Dry - Reheis) | 20 g | 20 g |
| Zinc pidolate | 0.05 g | 1 g |
| Stearyl alcohol | — | 14 g |
| PEG-8 distearate (PEG 400 distearate - Stearineries Dubois) | — | 2 g |
| C12-15 alkyl benzoate (Finsolv TN - Witco) | — | 15 g |
| | 100 | 100 |

The cyclopentasiloxane was heated to 65° C. The other ingredients were added (one by one) while keeping the temperature at 65°-70° C. The mixture was homogenized (transparent solution) for 15 minutes. The two deodorant active agents and the talc were added. The resulting mixture was cooled to about 55° C. (a few degrees Celsius above the thickening of the mixture) and was cast into sticks. The sticks were placed at 4° C. for 30 minutes.

The deposit of white residue of Formulations 3 and 4 after application was measured according to the test described below.

Protocol

The measurement was performed using a Minolta CR300 machine. The products were applied by rubbing back and forth until about 1 g of product per 40 cm² was obtained on a black paper of Canson mid-tint sheet type. The measurement was performed immediately after application. An average of two measurements was taken.

A delta L was measured: $\Delta L = L^*\text{product} - L^*\text{reference}$.

$L^*$reference of the black paper of Canson mid-tint sheet type: $L^*\text{reference} = 19.45$.

It was estimated that a product is whitening and cosmetically unacceptable for a $\Delta L$ of greater than 35.

The results obtained were summarized in the following table:

| Formulation | ΔL |
|---|---|
| 5 (prior art) | 35 |
| 6 (invention) | 6 |

It was found that Formulation 5 according to the prior art containing the zinc pidolate/aluminum chlorohydrate combination in a 1/400 ratio produced a high level of white residue on the substrate, whereas Formulation 6 according to the present disclosure produced very little white residue, comparable with the deodorant sticks currently on the market, such as the commercial products "Lady Speed Stick—Clean Glide" from Colgate or "Secret Clear Dry" from Procter & Gamble.

Formulation 7: Roll-on (Emulsion)

| Phase | Ingredients | Formulation 7 |
|---|---|---|
| A | Aluminum chlorohydrate (50% solution) (Chlorhydrol 50% USP) | 40 g |
|   | Zinc pidolate | 4 g |
| B | Steareth-21 (Brij 721 - ICI) | 2 g |
|   | Steareth-2 (Brij 2 - ICI) | 2 g |
|   | Steareth-5 Stearate | 1 g |
|   | PPG-15 stearyl ether (Arlamol E - ICI) | 1.5 g |
|   | Cyclopentasiloxane (DC245 - Dow Corning) | 3.5 g |
| C | Water | 47 g |
|   |   | 100 g |

Phases (B) and (C) were heated separately to 70° C. Phases (B) and (C) were mixed together using a Turrax stirrer for 5 minutes and then cooled to 55° C. with paddle stirring. Phase (A) was added slowly with stirring. The mixture was homogenized for 1 to 3 minutes. It was cooled to 35° C. with stirring. The formulation was stable for 2 months at 45° C.

The amount of white residue was measured according to the same test as described in Formulations 3 and 4. A $\Delta L$ equal to 2 was obtained.

Formulation 8: Non-aerosol Spray (Emulsion Obtained by Phase Inversion)

| Ingredients | Formulation 8 |
|---|---|
| Aluminum chlorohydrate (50% solution) (Chlorhydrol 50% USP) | 20 g |
| Zinc pidolate | 3 g |
| Cetearyl isononanoate (and) Cetearyl alcohol (and) Ceteareth-20 (and) Glycerin (and) Glyceryl stearate (and) Ceteareth-12 (and) cetyl palmitate (Emulgade CM - Cognis) | 15 g |
| Water | 63 g |
|   | 100 g |

The pidolate was dissolved in water and the Emulgade CM was added with moderate stirring. The aluminum salt solution was added with moderate stirring. The formulation was stable for 2 months at 45° C. The amount of white residue was measured according to the same test as described with regard to Formulations 5 and 6. A $\Delta L$ equal to 0 was obtained.

Formulation 9: Aerosol

| Ingredients | Formulation 9 |
|---|---|
| Stearalkonium Bentonite (Tixogel MP 250 - Sud Chemie Rheologicals United Catalysts Inc.) | 0.5 g |
| Aluminum chlorohydrate (Micro Dry - Reheis) | 7 g |
| Zinc pidolate | 1 g |
| $C_{12\text{-}15}$ alkyl benzoate (Finsolv TN - Witco) | 3 g |
| Isobutane | 80 g |
| Triethyl citrate (Citroflex-Morflex) | 1 g |
| Isopropyl palmitate | 1 g |
| Cyclopentasiloxane (DC245 - Dow Corning) | 6.5 g |
|   | 100 g |

The solvents and the hydrophobic-modified clay were introduced and the mixture was then stirred using a Turrax stirrer until homogenized. The aluminum salt (antiperspirant) and the zinc pidolate were then added with continued stirring. The propellant was then introduced in a conventional manner. The level of white residue was measured according to the same test as described with regard to Formulations 5 and 6. A $\Delta L$ equal to 4 was obtained for Formulation 9.

What is claimed is:

1. A composition comprising a) zinc pidolate and b) at least one antiperspirant aluminum salt, wherein the zinc pidolate/at least one aluminum salt weight ratio ranges from 1/200 to 10/1.

2. The composition according to claim 1, wherein the zinc pidolate/at least one aluminum salt weight ratio ranges from 1/20 to 5/1.

3. The composition according to claim 1, wherein the at least one antiperspirant aluminum salt is chosen from aluminum halohydrates; aluminum zirconium halohydrates; and complexes of zirconium hydroxychloride and of aluminum hydroxychloride with an amino acid.

4. The composition according to claim 3, wherein the at least one antiperspirant aluminum salt is chosen from aluminum chlorohydrate in activated and unactivated form, aluminum chlorohydrex, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichlorohydrate, aluminum sesquichlorohydrex polyethylene glycol complex, aluminum sesquichlorohydrex propylene glycol complex, and aluminum sulfate buffered with sodium aluminum lactate.

5. The composition according to claim 3, wherein the at least one antiperspirant aluminum salt is chosen from aluminum zirconium octachlorohydrate, aluminum zirconium pentachlorohydrate, aluminum zirconium tetrachlorohydrate, and aluminum zirconium trichlorohydrate.

6. The composition according to claim 3, wherein the at least one antiperspirant aluminum salt is chosen from complexes of zirconium hydroxychloride, and of aluminum hydroxychloride with glycine.

7. The composition according to claim 6, wherein the at least one antiperspirant aluminum salt is chosen from aluminum zirconium octachlorohydrex glycine, aluminum zirconium pentachlorohydrex glycine, aluminum zirconium tetrachlorohydrex glycine, and aluminum zirconium trichlorohydrex glycine complexes.

8. The composition according to claim 1, wherein the at least one antiperspirant aluminum salt is chosen from aluminum chlorohydrate in activated and unactivated form.

9. The composition according to claim 1, wherein the at least one antiperspirant aluminum salt is present in an amount ranging from 0.5% to 25%, by weight relative to the total weight of the composition.

10. The composition according to claim 1, wherein the zinc pidolate is present in an amount ranging from 0.05% to 10%, by weight relative to the total weight of the composition.

11. The composition according to claim 10, wherein the zinc pidolate is present in an amount ranging from 0.1% to 5%, by weight relative to the total weight of the composition.

12. The composition according to claim 1, wherein the composition is in a form chosen from a lotion; a cream and a fluid gel distributed as an aerosol spray, in a pump-dispenser bottle and as a roll-on; a cream and gel distributed in a tube and grille; and a wand (stick).

13. The composition according to claim 1, further comprising at least one aqueous phase.

14. The composition according to claim 13, wherein the composition is in the form of an aqueous lotion, wherein the aqueous lotion is in the form chosen from a water-in-oil emulsion, an oil-in-water emulsion, and a multiple emulsion.

15. The composition according to claim 13, wherein the at least one aqueous phase comprises water and at least water-soluble or water-miscible solvent.

16. The composition according to claim 14, wherein the at least one water-soluble or water-miscible solvent is chosen from $C_1$-$C_4$ monoalcohols, diols, and polyols.

17. The composition according to claim 1, wherein the composition is anhydrous.

18. The composition according to claim 1, further comprising at least one water-immiscible organic liquid phase.

19. The composition according to claim 18, wherein the at least one water-immiscible organic liquid comprises at least one emollient oil chosen from volatile and non-volatile silicone-based, and hydrocarbon-based emollient oils.

20. The composition according to claim 19, wherein the at least one emollient oil is present in an amount ranging from 1% to 50%, by weight relative to the total weight of the composition.

21. The composition according to claim 20, wherein the at least one emollient oil is present in an amount ranging from 5% to 40%, by weight relative to the total weight of the composition.

22. The composition according to claim 1, further comprising at least one additional deodorant active agent.

23. The composition according to claim 22, further comprising at least one additional bacteriostatic agent or bactericidal agent.

24. The composition according to claim 1, further comprising at least one suspension agent.

25. The composition according to claim 1, further comprising at least one organic powder.

26. The composition according to claim 1, further comprising at least one cosmetic additive chosen from waxes, softeners, antioxidants, opacifiers, stabilizers, moisturizers, vitamins, fragrances, bactericides, preserving agents, polymers, fragrances, thickeners, and propellants.

27. The composition according to claim 18, further comprising at least one agent for structuring or gelling the at least one water-immiscible organic liquid phase.

28. An aerosol device comprising a container comprising a deodorant composition comprising a) zinc pidolate and b) at least one antiperspirant aluminum salt, wherein the zinc pidolate/at least one aluminum salt weight ratio ranges from 1/200 to 10/1; at least one propellant; and a device for distributing the aerosol composition.

29. A cosmetic process for treating human underarm odors comprising applying to the underarm area an effective amount of a deodorant composition comprising a) zinc pidolate and b) at least one antiperspirant aluminum salt, wherein the zinc pidolate/at least one aluminum salt weight ratio ranges from 1/200 to 10/1.

* * * * *